United States Patent
Seamans et al.

(10) Patent No.: US 7,542,541 B2
(45) Date of Patent: Jun. 2, 2009

(54) VIEW WEIGHTING METHODS AND APPARATUS

(75) Inventors: John Lawrence Seamans, Grand Rapids, MI (US); Xingyang Tang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/551,611

(22) Filed: Oct. 20, 2006

(65) Prior Publication Data

US 2008/0101531 A1 May 1, 2008

(51) Int. Cl.
  *A61B 6/00* (2006.01)
(52) U.S. Cl. .............................. 378/8; 378/4
(58) Field of Classification Search ............. 378/4–20, 378/901
  See application file for complete search history.

(56) References Cited

U.S. PATENT DOCUMENTS

| | | | |
|---|---|---|---|
| 4,991,189 A | | 2/1991 | Boomgaarden et al. |
| 5,251,128 A * | | 10/1993 | Crawford ..................... 600/425 |
| 5,262,946 A * | | 11/1993 | Heuscher ..................... 378/15 |
| 5,671,263 A * | | 9/1997 | Ching-Ming ................... 378/8 |
| 5,832,051 A * | | 11/1998 | Lutz ............................. 378/8 |
| 6,101,236 A * | | 8/2000 | Wang et al. ..................... 378/4 |
| 6,154,516 A * | | 11/2000 | Heuscher et al. ............... 378/15 |
| 6,226,350 B1 * | | 5/2001 | Hsieh ........................... 378/98 |
| 6,243,437 B1 * | | 6/2001 | Hu et al. ......................... 378/8 |
| 6,327,325 B1 * | | 12/2001 | Hsieh ............................. 378/4 |
| 6,421,552 B1 * | | 7/2002 | Hsieh ........................... 600/425 |
| 6,507,633 B1 * | | 1/2003 | Elbakri et al. ................... 378/8 |
| 6,522,712 B1 * | | 2/2003 | Yavuz et al. ..................... 378/4 |
| 6,539,074 B1 * | | 3/2003 | Yavuz et al. ..................... 378/4 |
| 6,628,981 B2 * | | 9/2003 | Baker et al. .................. 600/425 |
| 6,754,298 B2 * | | 6/2004 | Fessler .......................... 378/4 |
| 6,765,983 B2 | | 7/2004 | Yan et al. |
| 6,816,565 B1 * | | 11/2004 | Tang ............................ 378/15 |
| 6,879,655 B2 * | | 4/2005 | Proksa ............................ 378/4 |
| 6,937,690 B2 * | | 8/2005 | Bruder et al. ................. 378/15 |
| 6,956,926 B2 | | 10/2005 | Cesmeli et al. |
| 7,042,975 B2 * | | 5/2006 | Heuscher ....................... 378/8 |
| 7,054,475 B2 | | 5/2006 | Edic et al. |
| 7,079,618 B2 * | | 7/2006 | Tsuyuki ......................... 378/8 |
| 2003/0142778 A1 * | | 7/2003 | Proksa ............................ 378/4 |
| 2004/0017881 A1 * | | 1/2004 | Cesmeli et al. ................. 378/4 |
| 2004/0114708 A1 * | | 6/2004 | Bruder et al. ................... 378/4 |
| 2004/0120449 A1 * | | 6/2004 | Edic et al. ....................... 378/4 |
| 2004/0252806 A1 * | | 12/2004 | Taguchi et al. ................. 378/4 |
| 2005/0267348 A1 * | | 12/2005 | Wollenweber et al. ....... 600/407 |
| 2007/0053483 A1 * | | 3/2007 | Nagata et al. ................... 378/8 |

OTHER PUBLICATIONS

Manzke et al., Artifact Analysis and Reconstruction Improvement in Helical Cardiac Cone Beam CT, IEEE Transactions on Medical Imaging, vol. 23, No. 9, Sep. 2004, pp. 1150-1164.*

Koken et al., Aperture Weighted Cardiac Reconstruction for Cone-beam CT, Physics in Medicine and Biology, 51, 2006, pp. 3433-3448.*

(Continued)

*Primary Examiner*—Edward J Glick
*Assistant Examiner*—Alexander H Taningco
(74) *Attorney, Agent, or Firm*—Fisher Patent Group, LLC; Thomas M. Fisher

(57) ABSTRACT

A method includes performing a patient dependent view weighting of scan data.

19 Claims, 4 Drawing Sheets

OTHER PUBLICATIONS

Hoffmann et al., Noninvasive Coronary Angiography with 16-Dectector Row CT: Effect of Heart Rate, Radiology, 234, pp. 86-97.*

Elbakri, Statistical Reconstruction Algorithms for Polyenergetic X-ray Computed Tomography, University of Michigan, 2003, pp. 1-175.*

* cited by examiner

Increased range of views based on duration of cardiac rest period

US 7,542,541 B2

VIEW WEIGHTING METHODS AND APPARATUS

BACKGROUND OF THE INVENTION

This invention relates generally to diagnostic imaging methods and apparatus, and more particularly, to methods and apparatus that provide for tomographic reconstruction view weighting methods and apparatus.

In the past, image quality in cardiac CT (Computed Tomography) imaging has been fundamentally limited by temporal resolution of the system. For nearly all patients and heart rates, temporal resolution proved to be the limiting factor in evaluation of cardiac structures and assessment of coronary artery stenosis. Half-scan reconstruction algorithms sought to maximize temporal resolution at the expense of spatial resolution and contrast to noise characteristics in the images. Based on sampling theory, projection views from at least 180 degrees must be used to properly reconstruct an image without aliasing artifacts.

As the temporal resolution of CT systems has increased, some low heart rate exams are now no longer temporal resolution-limited. This trend will only continue as the temporal resolution of CT systems is increased. For instance, using an ECG-gated half-scan reconstruction technique with a rotation speed of 0.35 sec, a temporal resolution of 227 ms or greater can be achieved. Based on analysis in the literature, the rest period duration of the coronary arteries at low heart rates can be up to 300-400 ms. In these patients, diagnosis may not be limited by temporal resolution in the images, but by spatial resolution and noise limitations. For certain patients, it makes sense to balance the temporal, spatial, and noise characteristics in the image. This can be achieved by applying a patient-adaptive partial-scan reconstruction technique as described below.

BRIEF DESCRIPTION OF THE INVENTION

In one aspect, a method includes performing a patient dependent view weighting of scan data.

In another aspect, a method includes performing a patient adaptive view weighting of scan data.

In another aspect, a computer readable medium is embedded with a program configured to instruct a computer to perform a patient dependent view weighting of scan data.

In still another aspect, a system includes an energy source, an energy detector positioned to receive energy emitted from the source, and a computer operationally coupled to the detector, wherein the computer is configured to perform a patient dependent view weighting of scan data.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to other diagnostic imaging systems and modalities such as PET, SPECT, fused systems such as a CT/PET system, and/or any modality yet to be developed in which view weighting may be performed.

Figure 1:
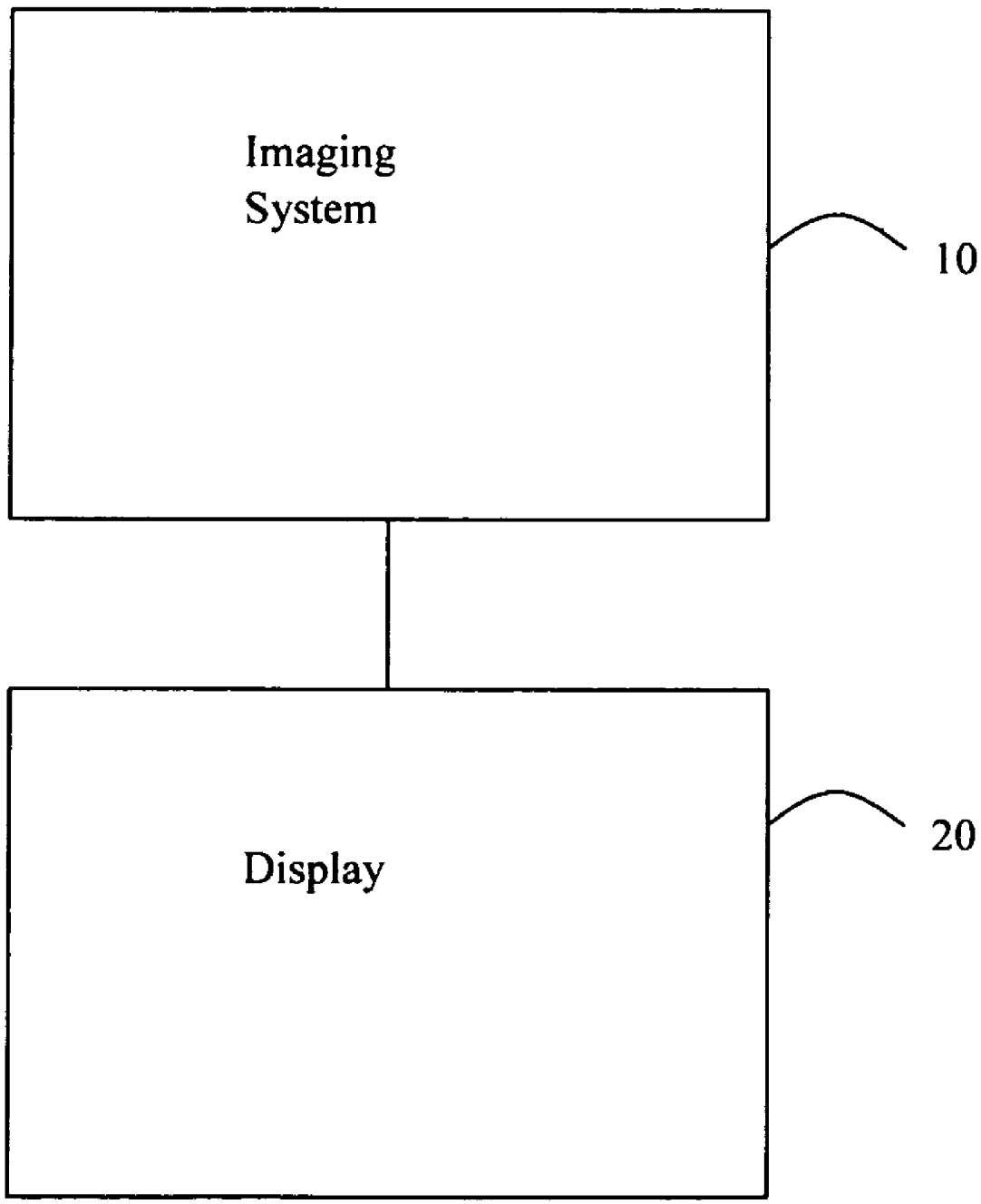
FIG. 1 illustrates an exemplary diagnostic imaging system.

FIG. 1 illustrates an imaging system 10 with an associated display 20. Imaging system 10 can be of any of the above mentioned modalities, but in one embodiment, system 10 is a CT system. In another embodiment, system 10 is a dual modality imaging system such as a combined CT/PET system and the below described view weighting can be done in one modality (e.g., CT) and the processed data can be transferred to the other modality (e.g., PET). Display 20 can be separate from system 10 or integrated with system 10. System 10 includes an acquisition device such as an x-ray radiation detector, or a Gamma Camera. In all the above modalities, please note that there is energy traveling at least partially through at least one component of a body and impinging an energy detector. A computer is coupled to the detector for processing the received data and producing an image if desired.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector. It is contemplated that the benefits of patient dependent and or patient adaptive view weighting accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two dimensional slice taken through the object. One method for reconstructing an image from a set of projection data is referred to in the art as the filtered back projection technique. Transmission and emission tomography reconstruction techniques also include statistical iterative methods such as Maximum Likelihood Expectation Maximization (MLEM) and Ordered-Subsets Expectation-Maximization (OSEM). The view-weighting techniques described herein can be applied to filtered back-projection reconstruction techniques as well as iterative reconstruction techniques. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

The patient-adaptive (retrospective) cardiac image reconstruction technique can make use of an accurate estimation of the cardiac rest period for each heart cycle during a patient's CT exam. The rest period is defined as the period of relative motionlessness of the heart, during end diastole or end systole of the cardiac cycle. The effective rest period for a given heart cycle can be determined by analyzing tomographic images over small cardiac phase increments using half-scan reconstruction techniques (maximum temporal resolution). This can also be achieved by other means—including, but not limited to: mechanical gating signals which accurately record the cardiac rest period, simultaneous echocardiography during the CT exam, and advanced ECG signal analysis. After the effective rest period for each heart beat of the patient's exam has been determined, the exam can be reconstructed using a patient-adaptive partial scan view weighting based on the quiescent period that has been determined for each heart cycle. The range of view angles used for the reconstruction is extended to optimize use of the views throughout the patient's cardiac rest period in each heart cycle. The range of projection view angles used for image reconstruction of images is adapted on a per-heartbeat, per-patient basis. This range can be anywhere between 180 and 360 degrees of views in parallel ray geometry. In practice, with a 30 degree fan angle in cone-beam geometry, 180 degrees+2*30 degree fan=240 degrees of views are commonly used for image reconstruction, so partial scan recon can be done with range of view angles between 240 and 420 degrees. This extends the range of views beyond the currently used 180 degree+2*fan angle based on the duration of each individual patient's cardiac rest period.

When partial-scan and corresponding view weighting techniques are employed in a gated helical acquisition, the helical pitch should be decreased accordingly to keep cone beam and helical artifacts as minimum as possible. If axial snap shot mode (also know as a "step-and-shoot" or "Snap Shot Cine" acquisition) is utilized, the pitch is no longer an issue, since use of a wider range of view angles will not create any cone beam or helical artifacts.

The resulting images take advantage of the lower temporal resolution requirements at lower heart rates (due to the increased cardiac/coronary artery rest periods) to create high-resolution, low-noise cardiac images. This technique still allows for maximum temporal resolution when it is needed at high heart rates.

Figure 2:
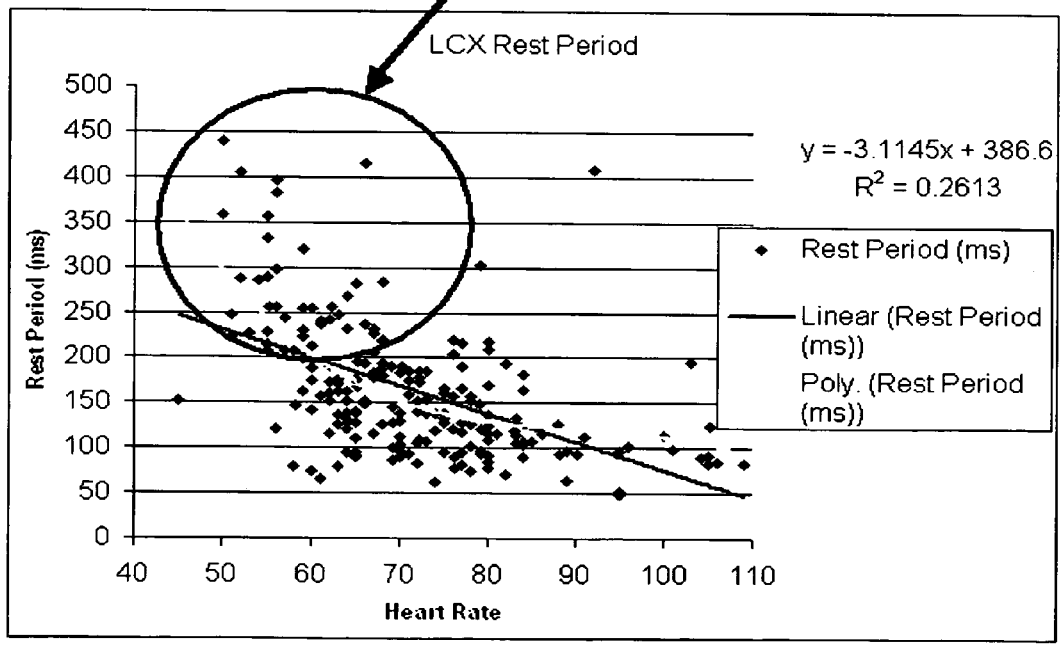
FIG. 2 illustrates a graph of Cardiac Rest Period Distribution vs. Heart Rate. (VCT Half Scan Temporal Res~227 ms).

FIG. 2 illustrates a graph of Cardiac Rest Period Distribution vs. Heart Rate, wherein the raw data comes from Jahnke C, Paetsch I, et al. Coronary MR Imaging: Breath-hold Capability and Patterns, Coronary Artery Rest Periods. Radiology 2006. Note that cardiac image quality for patients identified in the graph could be improved with an adaptive partial-scan view weighting technique, based on the temporal resolution of present-day CT scanners (for example, VCT has a temporal resolution of approximately 227 ms in cardiac helical mode). Note that, in FIG. 2, LCX=left circumflex artery.

Figure 3:
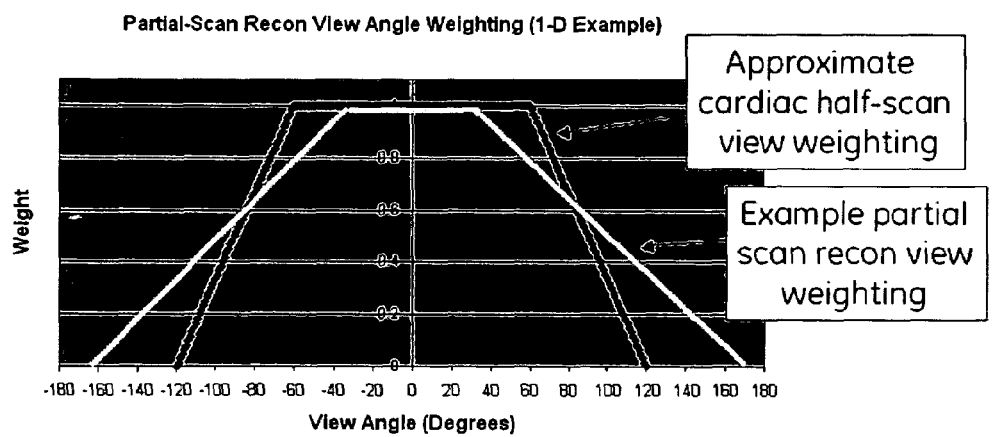
FIG. 3 illustrates a simplified representation of current cardiac half-scan view weighting, and an adaptive view weighting based on patient rest period duration.

FIG. 3 illustrates a simplified representation of current cardiac half-scan view weighting in Cone-Parallel Geometry, and an adaptive view weighting based on patient rest period duration.

Figure 4:
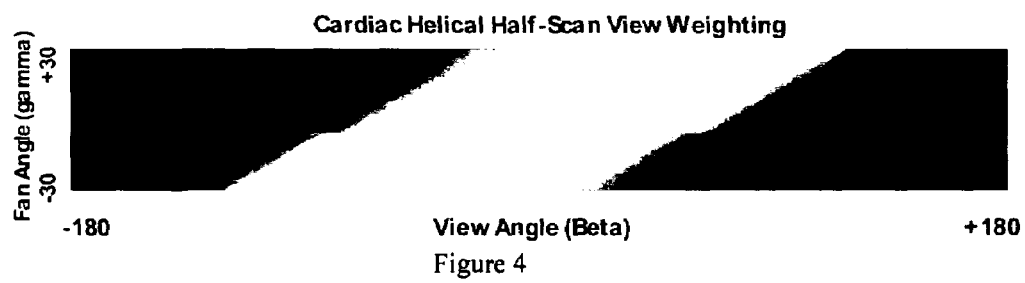
FIG. 4 illustrates one embodiment of a cardiac helical half-scan view weighting.

FIG. 4 illustrates one embodiment of a cardiac helical half-scan view weighting in the Native Cone Beam Geometry. In one embodiment, FIG. 4 is an approximation.

Figure 5:
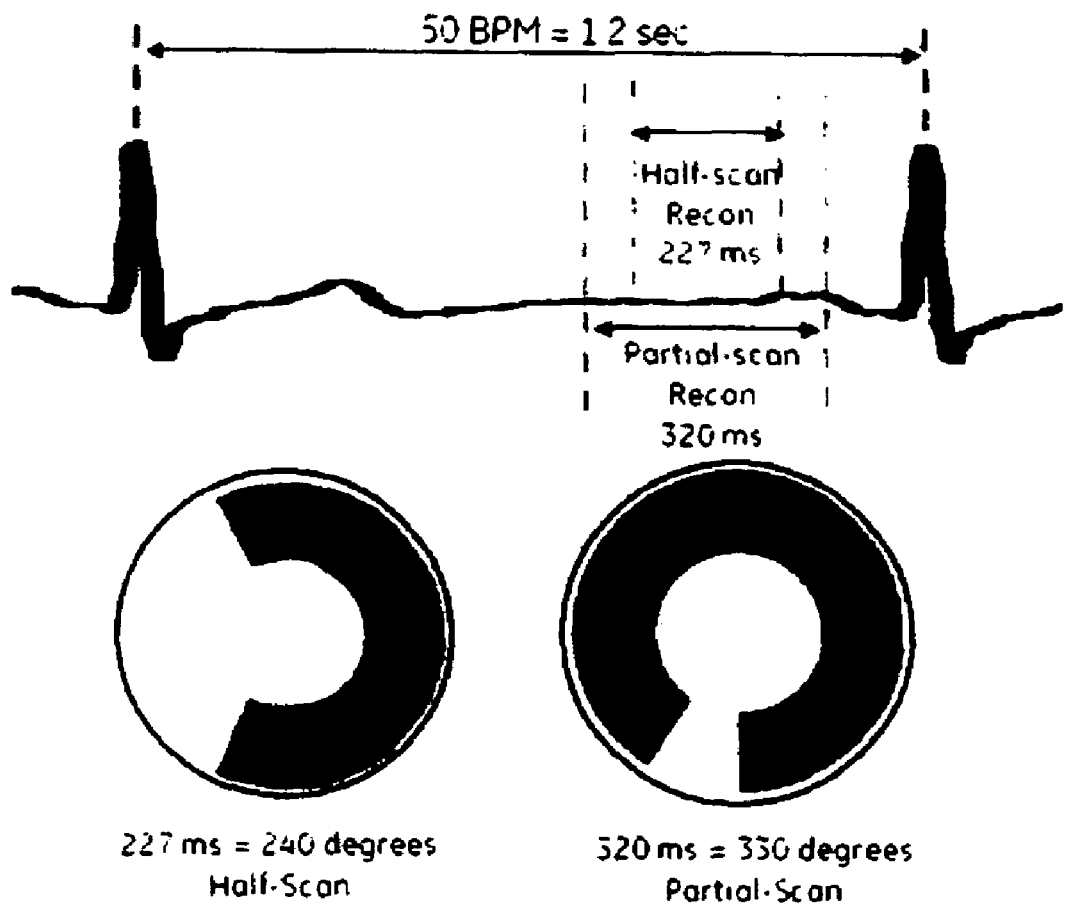
FIG. 5 illustrates an example of a partial-scan reconstruction based on rest period duration of a given cardiac cycle (50 BPM, 0.35 sec/rotation.).

FIG. 5 illustrates an example of a partial-scan reconstruction based on rest period duration of a given cardiac cycle (50 BPM, 0.35 sec/rotation.). The figure shows an example range of views used for standard half-scan recon (not modified on a per-patient basis) and patient-adaptive partial scan recon, which utilizes view data acquired during the full duration of the rest period of the current cardiac cycle.

Technical effects include that the herein described methods and apparatus will optimize the temporal resolution, spatial resolution, and noise image quality tradeoffs on a per-patient basis. For exams that can utilize this technique (patients with cardiac rest periods>system temporal resolution), there will be improvements in spatial resolution, SNR (signal to noise ratio), and CNR (contrast to noise ratio).

The view weighting is patient and heart cycle-dependant. By heart cycle dependent, the view weighting is patient adaptive. As used herein, the term "patient dependent" refers to using different view weighting for different patients based on a patient parameter during the scan such as for example the number of beats per minute (BPM). As used herein the term "patient adaptive" refers to using different view weighting for different parts of a scan(s) of a single patient based on a patient parameter during the scan such as for example the BPM. For example, a patient may start an exam at 50 BPM and later towards the end of the exam the BPM may have increased to 55, and the view weighting adjusts to the change to BPM. Of course, the BPM may decrease and the view weighting adapts to the decrease as well.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising performing a patient dependent view weighting of scan data and a patient adaptive view weighting of scan data in response to a change in beats per minute of the patient's heart in a statistical iterative reconstruction technique and where the patient has cardiac rest periods greater than a system temporal resolution.

2. A method in accordance with claim 1 wherein the scan data is of a heart.

3. A method in accordance with claim 1 wherein the scan data is quiescent data of a heart.

4. A method in accordance with claim 1 wherein the scan data is from a half-scan.

5. A method in accordance with claim 1 wherein the scan data is from a partial scan that contains greater than 180 degrees of view data but less than 360 degrees.

6. A method in accordance with claim 5 wherein the scan is at least 240 degrees.

7. A method in accordance with claim 1 wherein the scan data is from a CT scan.

8. A method in accordance with claim 1 wherein the scan data is quiescent data of a heart.

9. A method in accordance with claim 1 wherein the scan data is from a CT scan.

10. A method in accordance with claim 1 where the statistical iterative reconstruction technique is a Maximum Likelihood Expectation Maximization (MLEM) technique.

11. A method in accordance with claim 1 where the statistical iterative reconstruction technique is an Ordered-Subsets Expectation-Maximization (OSEM) technique.

12. A computer readable medium embedded with a program configured to instruct a computer to perform a patient dependent view weighting of scan data and a patient adaptive view weighting of scan data in response to a change in beats per minute of the patient's heart in a statistical iterative reconstruction technique and where the patient has cardiac rest periods greater than a system temporal resolution.

13. A medium in accordance with claim 12 wherein the program is also configured to instruct the computer to perform a patient adaptive view weighting of CT scan data.

14. A medium in accordance with claim 12 wherein the program is also configured to instruct the computer to perform a patient adaptive view weighting of CT scan data from a partial scan.

15. A system comprising:
an energy source;
an energy detector positioned to receive energy emitted from said source; and
a computer operationally coupled to said detector, said computer configured to perform a patient dependent view weighting of scan data and a patient adaptive view weighting of scan data in response to a change in beats per minute of the patient's heart in a statistical iterative reconstruction technique and where the patient has cardiac rest periods greater than a system temporal resolution.

16. A system in accordance with claim 15 wherein said computer further configured to perform a patient dependent view weighting of scan data comprising data of a moving object.

17. A system in accordance with claim 15 wherein said computer further configured to perform a patient dependent view weighting of scan data comprising data of a heart.

18. A system in accordance with claim 15 wherein said computer further configured to perform a patient dependent view weighting of scan data comprising data of a quiescent period of a heart.

19. A system in accordance with claim 15 wherein said computer further configured to perform a patient dependent view weighting of scan data comprising data from a partial scan.

* * * * *